United States Patent
Kim

(10) Patent No.: US 10,238,466 B2
(45) Date of Patent: Mar. 26, 2019

(54) METHOD OF MAKING A SUPERELASTIC MEDICAL DEVICE WITH A RADIOPAQUE MARKER

(71) Applicant: Cook Medical Technologies LLC, Bloomington, IN (US)

(72) Inventor: Woong Kim, West Lafayette, IN (US)

(73) Assignee: Cook Medical Technologies LLC, Bloomington, IN (US)

(*) Notice: Subject to any disclaimer, the term of this patent is extended or adjusted under 35 U.S.C. 154(b) by 98 days.

(21) Appl. No.: 15/623,917

(22) Filed: Jun. 15, 2017

(65) Prior Publication Data

US 2018/0360555 A1    Dec. 20, 2018

(51) Int. Cl.
| | |
|---|---|
| A61B 90/00 | (2016.01) |
| A61F 2/88 | (2006.01) |
| B23P 11/02 | (2006.01) |
| C22F 1/00 | (2006.01) |
| B23P 15/00 | (2006.01) |
| A61F 2/86 | (2013.01) |

(52) U.S. Cl.
CPC ............ *A61B 90/39* (2016.02); *B23P 11/025* (2013.01); *B23P 15/00* (2013.01); *C22F 1/006* (2013.01); *A61B 2090/3966* (2016.02); *A61B 2090/3983* (2016.02); *A61F 2/86* (2013.01); *A61F 2210/0014* (2013.01); *A61F 2240/001* (2013.01); *A61F 2250/0098* (2013.01)

(58) Field of Classification Search
CPC ................ A61F 2/88; A61F 2210/0014; A61F 2240/1001; A61F 2250/0098; A61B 90/39; A61B 2090/3966; A61B 2090/3983; B23P 11/025; B23P 15/00; C22F 1/006
See application file for complete search history.

(56) References Cited

U.S. PATENT DOCUMENTS

| | | | | |
|---|---|---|---|---|
| 5,437,282 | A * | 8/1995 | Koger | A61B 8/12 600/463 |
| 6,598,280 | B1 * | 7/2003 | Giba | A61M 25/0041 148/563 |
| 9,439,791 | B2 | 9/2016 | Vong et al. | |
| 2007/0021811 | A1 * | 1/2007 | D'Aquanni | A61L 29/085 607/119 |
| 2007/0219621 | A1 | 9/2007 | Hartley et al. | |
| 2008/0300673 | A1 * | 12/2008 | Clerc | A61F 2/90 623/1.15 |
| 2009/0177268 | A1 * | 7/2009 | Lundkvist | A61F 2/90 623/1.22 |

(Continued)

FOREIGN PATENT DOCUMENTS

WO    WO 2002/26410 A2    4/2002

*Primary Examiner* — Jermie Cozart
(74) *Attorney, Agent, or Firm* — Brinks Gilson & Lione

(57) ABSTRACT

A method of making a superelastic medical device with a radiopaque marker includes threading a radiopaque marker having an elongated shape over a wire comprising a shape memory alloy. After the threading, the wire is secured in a predetermined configuration to a mandrel. While secured to the mandrel, the wire is heat set in an environment comprising an inert gas so as to impart a memory of the predetermined configuration to the wire and superelastic properties to the shape memory alloy. A superelastic medical device including the radiopaque marker is thus formed.

20 Claims, 2 Drawing Sheets

(56) References Cited

U.S. PATENT DOCUMENTS

| | | | |
|---|---|---|---|
| 2009/0198315 A1* | 8/2009 | Boudjemline | A61F 2/2418 623/1.2 |
| 2012/0310319 A1* | 12/2012 | Tieu | A61F 2/852 623/1.4 |
| 2012/0330402 A1* | 12/2012 | Vad | A61F 2/07 623/1.13 |
| 2013/0110000 A1 | 5/2013 | Tully et al. | |
| 2013/0327450 A1 | 12/2013 | Green | |

* cited by examiner

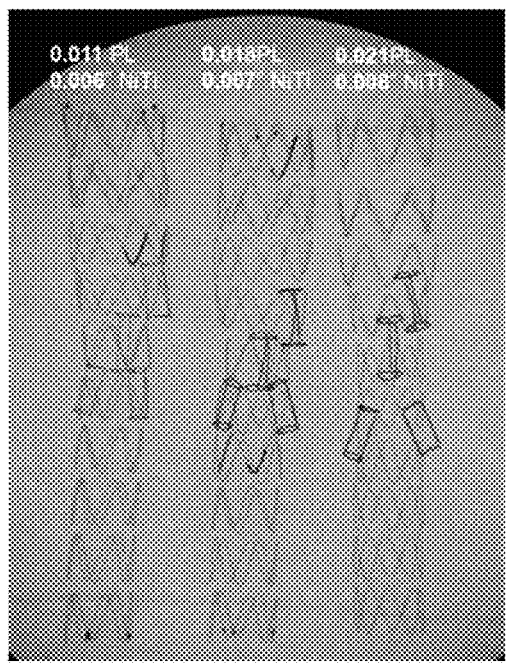
FIG. 3A   FIG. 3B   FIG. 3C      FIG. 4A   FIG. 4B   FIG. 4C

METHOD OF MAKING A SUPERELASTIC MEDICAL DEVICE WITH A RADIOPAQUE MARKER

TECHNICAL FIELD

The present disclosure is related generally to medical devices and more particularly to a method of fabricating an intraluminal medical device including a radiopaque marker.

BACKGROUND

A stent is a tubular support structure that may be implanted within a blood vessel or other body vessel to treat blockages, occlusions, narrowing ailments and other related problems that restrict flow through the vessel. When delivered to the site of a constricted vessel and expanded from a compressed configuration to an expanded configuration, the stent exerts a radial force on the vessel wall and prevents it from closing. Balloon-expandable stents expand in response to the inflation of a balloon, whereas self-expanding stents may deploy automatically when released from a delivery device. Self-expanding stents are often fabricated from superelastic or shape memory alloys that can "remember" and recover a previous shape.

In order to effectively treat blockages, occlusions and other ailments that restrict flow through a body vessel, it is important that the stent be precisely placed at the site of the constriction. One approach to achieve precise stent placement is to attach one or more radiopaque markers to the stent to permit visualization of the stent from outside the body using x-ray fluoroscopy. During the implantation procedure, the position of the markers—and thus the position of the stent—may be monitored using a fluoroscope. The x-ray visibility of stents made of metals such as nickel and titanium may be substantially improved by using markers formed from heavier metals such as platinum or gold, which produce higher x-ray contrast. Radiopaque markers may also be beneficial for improving the x-ray visibility of medical devices other than stents.

BRIEF SUMMARY

A method of making a superelastic medical device with a radiopaque marker includes threading a radiopaque marker having an elongated shape over a wire comprising a shape memory alloy. After the threading, the wire is secured in a predetermined configuration to a mandrel. While secured to the mandrel, the wire is heat set in an environment comprising an inert gas so as to impart a memory of the predetermined configuration to the wire and superelastic properties to the shape memory alloy. A superelastic medical device including the radiopaque marker is thus formed.

BRIEF DESCRIPTION OF THE DRAWINGS

FIGS. 3A-3C show images of exemplary endovascular stent graft devices with side branch ring stents threaded with radiopaque coils.

FIGS. 4A-4C show x-ray images of the stent graft devices of FIGS. 3A-3C, respectively.

DETAILED DESCRIPTION

An improved method of making a superelastic medical device that includes a radiopaque marker has been developed. The medical device is fabricated from a wire comprising a shape memory alloy that is formed and heat set into a desired configuration to fabricate a superelastic medical device. In contrast to prior art methods of attaching radiopaque markers to medical devices, the radiopaque marker is applied prior to heat setting, and the heat setting is carried out in an inert gas atmosphere. Thus, oxide formation on surfaces of the medical device can be avoided during heat-setting, and a post-heat setting electropolishing step may not be required. In addition, a laborious, post-heat setting process of applying the radiopaque marker to the medical device is not needed as in conventional methods. The new method is simple and less labor-intensive than alternative fabrication methods, and facilitates construction of medical devices of highly complex shapes with radiopaque markers that may span an entire length of the device.

Figure 1A:
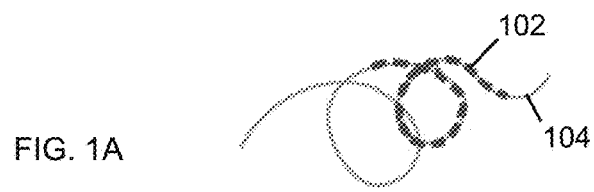
FIGS. 1A-1E are schematics showing steps of the method, according to one example.
Figure 1B:
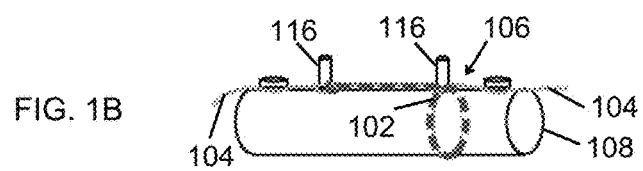
Figure 1C:
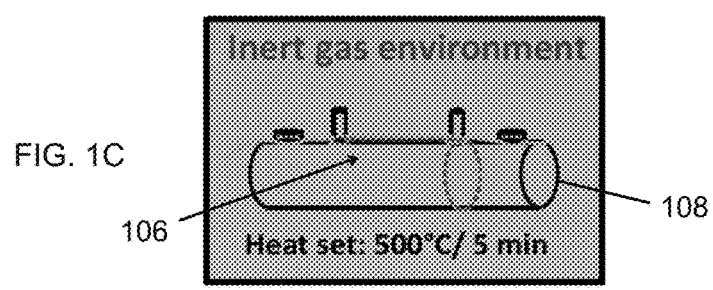

Referring to FIG. 1A, the method entails, prior to heat setting, threading a radiopaque marker 102 having an elongated shape over a wire 104 comprising a shape memory alloy, such as an equiatomic or near-equiatomic nickel-titanium alloy. After the threading, the wire 104 is secured in a predetermined configuration 106 to a mandrel 108, as illustrated in FIG. 1B. The wire 104 is then heat set in an atmosphere comprising an inert gas to impart a memory of the predetermined configuration 106 to the wire and superelastic properties to the shape memory alloy, as illustrated in FIG. 1C. The radiopaque marker 102 remains on the wire 104 during the heat setting process. A superelastic medical device 110 (e.g., a stent) including a radiopaque marker is formed as a consequence of the heat setting process. The predetermined configuration 106 of the wire on the mandrel 108 determines the shape of the superelastic medical device 110 formed from the method. For example, the predetermined configuration 106 may define a stent 112 in a radially expanded configuration. As shown in FIG. 1E, which is discussed further below, the stent 112 may be a side branch ring stent.

Figure 1D:
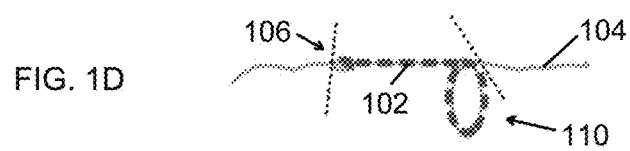
Figure 1E:
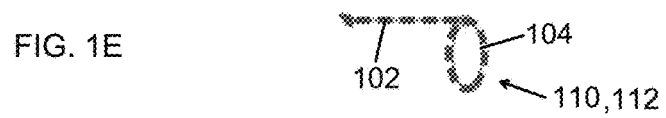

The method may further entail, after the heat setting, trimming one or more ends of the wire 104 extending beyond the predetermined configuration 106 that determines the shape of the superelastic medical device 110, as illustrated in FIG. 1D. The superelastic medical device 110 may also be removed from the mandrel 108 for further processing and/or intraluminal use.

The radiopaque marker 102 comprises a radiopaque and biocompatible material that strongly absorbs incident x-rays over a given energy range and tends to show high contrast and good visibility in x-ray images. Radiopaque materials that have both a high density and good biocompatibility include, for example, platinum, palladium, and gold. Accordingly, the radiopaque marker 102 employed in the method may comprise a radiopaque material such as platinum, palladium, and/or gold.

Figure 2:
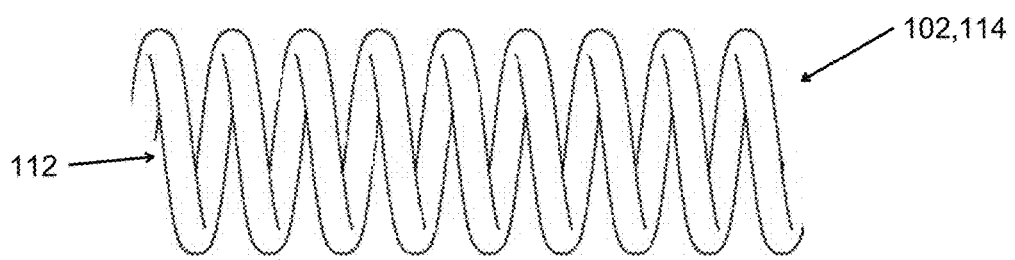
FIG. 2 is a schematic of a radiopaque coil that can be employed as a radiopaque marker in the method of FIGS. 1A-1E.

The radiopaque marker 102 comprises a through-hole 112 for threading over the wire 104. The elongated shape of the marker 102 may comprise a coiled shape, and the radiopaque marker may take the form of a radiopaque coil or spring 114, as shown in the schematic of FIG. 2. The radiopaque coil 114 typically has a wire diameter in a range from about 0.002" to about 0.01" (0.05 mm to about 0.25 mm), a coil diameter in a range from about 0.01" to about 0.05" (about 0.25 mm to about 1.3 mm), and a pitch in range from about 0.005″ to about 0.008″ (about 0.13 mm to about 0.20 mm). The wire 104 over which the radiopaque marker 102 (e.g., radiopaque coil 114) is threaded typically has a diameter from about 0.005″ to about 0.01″ (about 0.13 mm to about 0.25 mm). Suitable radiopaque coils 114 may be obtained commercially from any of a number of vendors, including, for example, Medicoil. The elongated shape may also or alternatively comprise a tubular shape, and the radiopaque marker may take the form of a radiopaque cladding or sheath. Due to the recoverable strain possible with shape memory (or superelastic) alloys in use, it is preferred that the radiopaque marker is free to move over the wire. An advantage of the radiopaque coil 114 is its inherent capability to adapt like a spring to changes in the shape and/or size of the underlying superelastic wire.

The radiopaque marker 102 may have a length ("marker length") of at least about 50% of a length of the wire, at least about 70% of the length of the wire, or at least about 90% of the length of the wire after any trimming of the end(s) is carried out. The radiopaque marker 102 may be cut to the desired marker length prior to application to the wire. Since the marker length may be comparable to the length of the wire 104 (after trimming), much or all of the superelastic medical device may have enhanced visibility under x-ray irradiation.

Referring again to the schematic of FIG. 1B, it can be seen that securing the wire 104 in the predetermined configuration 106 to the mandrel 108 may comprise winding the wire (a) about one or more pins 116 extending radially outward from the mandrel 108 and (b) along a pathway traversing a circumference of the mandrel 108. The pathway may be defined by locations of the pin(s) 116. The predetermined configuration 106 may include at least one bend or curve and, more typically, a plurality of bends or curves along the pathway, as determined by the locations of the pins 116. A benefit of the new method is that highly complex and/or tortuous configurations of the wire 104 may be employed to form the medical device 110, since the radiopaque marker 102 is threaded over the wire 104 before the wire 104 is secured to the mandrel 108 in the desired configuration 106. As is illustrated in FIG. 1C, the radiopaque marker is formed to include the at least one bend or curve (or plurality of bends or curves) as the wire is wound about the one or more pins and over the mandrel. In other words, after securing the wire to the mandrel, the elongated shape of the radiopaque marker may be a bent or curved elongated shape.

Typically, the wire 104 is a round wire with a substantially circular transverse cross-section, but the method is also applicable to flat wires having a substantially square or rectangular transverse cross-section. Advantageously, a surface of the wire 104 over which the radiopaque marker 102 is threaded may be substantially free of oxides. The wire 104 employed in the method may be an electropolished wire. Such electropolished wire is commercially available. Alternatively, the method may further comprise, prior to threading the radiopaque marker over the wire, electropolishing the wire using methods known in the art. Since the heat setting is carried out in an inert atmosphere, electropolishing is not required after heat setting for removal of surface oxides, such as nickel oxides in the case of nickel-titanium alloys.

As indicated above, the shape memory alloy may be an equiatomic or near-equiatomic nickel-titanium alloy ("nickel-titanium alloy") that exhibits superelastic and/or shape memory behavior after heat setting. In the case of nickel-titanium alloys, superelastic or shape memory behavior can occur when the alloy transforms from a lower temperature phase (martensite) to a higher temperature phase (austenite). Strain introduced in the alloy in the martensitic phase to achieve a shape change may be substantially recovered upon completion of the reverse phase transformation to austenite, allowing the alloy to return to a previous shape. Austenite is characteristically the stronger phase, and martensite may be deformed up to a recoverable strain of about 8%. The strain recovery may be driven by the application and removal of stress (superelastic effect) and/or by a change in temperature (shape memory effect). Such nickel-titanium alloys are commonly referred to as Nitinol or Nitinol alloys.

Nickel-rich compositions of the nickel-titanium alloy may be advantageous to ensure that the medical device exhibits superelastic behavior at body temperature. Accordingly, after heat setting, it may be beneficial for the nickel-titanium alloy to have an austenite start temperature $A_s$ below body temperature (e.g., 37° C.) and an austenite finish temperature $A_f$ at or below body temperature. Alternatively, if the nickel-titanium alloy is to remain martensitic during use in the body, the nickel-titanium alloy may have an austenite finish temperature $A_f$ above body temperature, and the austenite start temperature $A_s$ may also be above body temperature. As known to those of skill in the art, austenite start temperature ($A_s$) is the temperature at which a phase transformation to austenite begins upon heating for a nickel-titanium alloy exhibiting an austenitic phase transformation, and austenite finish temperature ($A_f$) is the temperature at which the phase transformation to austenite concludes upon heating. Martensite start temperature ($M_s$) is the temperature at which a phase transformation to martensite begins upon cooling for a nickel-titanium alloy exhibiting a martensitic phase transformation, and martensite finish temperature ($M_f$) is the temperature at which the phase transformation to martensite concludes upon cooling.

For example, the nickel-titanium alloy may have from greater than 50 at. % Ni to about 52 at. % Ni, or from about 50.6 at. % Ni to about 50.8 at. % Ni. Titanium and any incidental impurities may account for the balance of the nickel-titanium alloy. In some cases, the nickel-titanium alloy may also include a small amount of an additional alloying element (AAE) (e.g., from about 0.1 at. % AAE to about 10 at. % AAE) to enhance the superelastic or other properties of the nickel-titanium alloy. The additional alloying element may be a transition metal or rare earth metal. It may also or alternatively be advantageous for the nickel-titanium alloy to include boron.

As is known in the art, heat setting is a shape-setting heat treatment carried out to impart a "memory" of a desired configuration to a component (e.g., wire) comprising a shape memory alloy while the component is constrained in the desired configuration. The heat treatment may also serve to optimize the properties of the shape memory alloy and alter phase transformation temperatures (e.g., $A_f$, as discussed above). Typically, heat setting temperatures in a range from about 350° C. to about 550° C., or from about 450° C. to about 550° C., are employed. The duration of the heat setting may be from about 1 minute to about 30 minutes, and is typically about 5 minutes. In conventional methods, heat setting is carried out in an ambient environment (e.g., in air). In the present method, however, the heat setting is carried out in a controlled environment comprising an inert gas, such as argon, helium, or nitrogen. To obtain the controlled environment, a vacuum chamber may be backfilled with an inert gas, which may be maintained at a pressure from about 1 to about 3 psi, for example, during the heat setting process.

As indicated above, the predetermined configuration 106 of the wire 104 on the mandrel 108 determines the shape of the superelastic medical device 110 formed from the method. The superelastic medical device 110 may be a stent, a stent graft, a wire guide, a torqueable catheter, an introducer sheath, an orthodontic arch wire, a manipulation, retrieval, or occlusive device such as a grasper, a snare, a basket (e.g., stone extraction or manipulation basket), a vascular plug, an embolic protection filter or another device for intraluminal use in a human body.

FIGS. 3A-3C show exemplary endovascular stent graft devices with side branch ring stents threaded with radiopaque coils. Side branch ring stents are described in detail in U.S. Pat. No. 7,914,572, which issued on Mar. 29, 2011, and is hereby incorporated by reference in its entirety. The main body of the stent graft and the side branch ring stents are fabricated from nickel-titanium alloy wires. The radiopaque coils threaded over the nickel-titanium wires of the side branch ring stents are fabricated from platinum wires. Each stent graft includes nickel-titanium and platinum wires of different diameters. FIG. 3A shows a stent graft fabricated from a nickel-titanium wire of 0.006" in diameter which includes side branch ring stents comprising the same nickel-titanium wire and overlaid with a platinum coil of 0.003" in wire diameter (0.011" in coil diameter); FIG. 3B shows a stent graft fabricated from a nickel-titanium wire of 0.007" in diameter which includes side branch ring stents fabricated from the same nickel-titanium wire and overlaid with a platinum coil of 0.004" in wire diameter (0.018" in coil diameter); and FIG. 3C shows a stent graft fabricated from a nickel-titanium wire of 0.008" in diameter which includes side branch ring stents fabricated from the same nickel-titanium wire and overlaid with a platinum coil of 0.005" in wire diameter (0.021" in coil diameter). FIGS. 4A-4C show x-ray images of the stent graft devices of FIGS. 3A-3C, respectively, where the devices show increasing x-ray contrast from left to right due to the presence of the thicker platinum coil employed in successive devices. As is apparent from viewing the x-ray images, use of the threaded radiopaque coils can be a highly effective method of providing visual information of location and orientation of the branches for visceral arteries. The physician can use pseudo-3D x-ray images of side branches to align the stent graft during deployment and subsequent cannulation for additional bridging stents.

Although the present invention has been described in considerable detail with reference to certain embodiments thereof, other embodiments are possible without departing from the present invention. The spirit and scope of the appended claims should not be limited, therefore, to the description of the preferred embodiments contained herein. All embodiments that come within the meaning of the claims, either literally or by equivalence, are intended to be embraced therein.

Furthermore, the advantages described above are not necessarily the only advantages of the invention, and it is not necessarily expected that all of the described advantages will be achieved with every embodiment of the invention.

The invention claimed is:

1. A method of making a superelastic medical device with a radiopaque marker, the method comprising:
   threading a radiopaque marker having an elongated shape over a wire comprising a shape memory alloy;
   after the threading, securing the wire in a predetermined configuration to a mandrel;
   heat setting the wire while secured to the mandrel in an environment comprising an inert gas so as to impart a memory of the predetermined configuration to the wire and superelastic properties to the shape memory alloy, thereby forming a superelastic medical device including the radiopaque marker.

2. The method of claim 1, wherein the radiopaque marker comprises a through-hole for threading over the wire.

3. The method of claim 1, wherein the elongated shape comprises a coiled shape, the radiopaque marker comprising a radiopaque coil.

4. The method of claim 1, wherein the elongated shape comprises a tubular shape, the radiopaque marker comprising a radiopaque cladding.

5. The method of claim 1, wherein the radiopaque marker comprises a radiopaque material selected from the group consisting of gold, platinum and palladium.

6. The method of claim 1, wherein the radiopaque marker is free to move over the wire.

7. The method of claim 1, wherein, after heat setting and any trimming of the wire, the radiopaque marker has a length of at least about 50% of a length of the wire.

8. The method of claim 7, wherein the length of the radiopaque marker is at least about 70% of the length of the wire.

9. The method of claim 1, wherein a surface of the wire over which the radiopaque marker is threaded is substantially free of oxides, the wire being an electropolished wire.

10. The method of claim 1, further comprising, prior to threading the radiopaque marker over the wire, electropolishing the wire.

11. The method of claim 1, wherein securing the wire in the predetermined configuration to the mandrel comprises:
    winding the wire about one or more pins extending radially outward from the mandrel and along a pathway traversing a circumference of the mandrel.

12. The method of claim 1, wherein the predetermined configuration includes at least one bend or curve along the pathway, and
    wherein, after the securing of the wire to the mandrel in the predetermined configuration, the radiopaque marker includes the at least one bend or curve, the elongated shape of the radiopaque marker being a bent or curved elongated shape.

13. The method of claim 1, wherein the inert gas is selected from the group consisting of argon, helium and nitrogen, and
    wherein the environment is maintained at an inert gas pressure ranging from about 1 psi to about 3 psi.

14. The method of claim 1, wherein the heat setting is carried out at a temperature in a range from about 450° C. to 550° C.

15. The method of claim 1, wherein, after the heat setting, the wire is not electropolished.

16. The method of claim 1, further comprising, after the heat setting, trimming one or more ends of the wire extending beyond the predetermined configuration.

17. The method of claim 1, further comprising, after the heat setting, removing the superelastic medical device from the mandrel.

18. The method of claim 1, wherein the superelastic medical device is selected from the group consisting of a stent, a stent graft, a wire guide, a torqueable catheter, an introducer sheath, an orthodontic arch wire, a grasper, a snare, a basket, a vascular plug, and an embolic protection filter.

19. The method of claim 18, wherein the superelastic medical device is a side branch ring stent.

20. The method of claim 1, wherein the shape memory alloy comprises a nickel-titanium alloy, and
wherein, after heat setting, the nickel-titanium alloy has an austenite finish temperature ($A_f$) at or below body temperature.

* * * * *